United States Patent
Schlama et al.

(10) Patent No.: US 6,800,784 B1
(45) Date of Patent: Oct. 5, 2004

(54) PROCESS FOR PREPARING A POLYAROMATIC COMPOUND

(75) Inventors: Thierry Schlama, Dardilly (FR); Jean-Christophe Bigouraux, Dargoire (FR)

(73) Assignee: Rhodia Chimie, Boulogne Billancourt Cedex (FR)

( * ) Notice: Subject to any disclaimer, the term of this patent is extended or adjusted under 35 U.S.C. 154(b) by 0 days.

(21) Appl. No.: 10/130,656

(22) PCT Filed: Nov. 24, 2000

(86) PCT No.: PCT/FR00/03289

§ 371 (c)(1),
(2), (4) Date: Sep. 3, 2002

(87) PCT Pub. No.: WO01/38291

PCT Pub. Date: May 31, 2001

(30) Foreign Application Priority Data

Nov. 26, 1999 (FR) ............................................ 99 14912

(51) Int. Cl.⁷ ...................... C07C 211/45; C07C 209/68
(52) U.S. Cl. ...................................... 564/307; 546/311
(58) Field of Search ........................... 564/307; 546/311

(56) References Cited

PUBLICATIONS

Stavenuiter et al., "Palladium–catalyzed cross–coupling of phenylboronic acid with heterocyclic aromatic halides" Heterocycles, 26(10), 1987, p. 2711–2716.*

Miura et al., "A convenient and efficient synthesis of polyphenylmon–, –di–and –triaminobenzenes" Syntheis, 1995, p. 1419–1422.*

W.J. Thomson et al.: "An efficient synthesis of arylpyrazines in bipyridines" Journal of Organic Chemistry, vol. 53, 1988, pp. 2052–2055, XP002143541, Easton US, pp. 2052–2054.

International Search Report.

* cited by examiner

*Primary Examiner*—Brian J. Davis

(57) ABSTRACT

The present invention concerns a process for preparing a polyaromatic compound comprising a concatenation of two aromatic cycles and carrying at least one amino group on one of the aromatic cycles. The process of the invention is characterized in that it consists of reacting an aromatic compound carrying at least one amino group and a leaving group with an arylboronic acid in an aqueous medium and in the presence of a palladium catalyst.

33 Claims, No Drawings

PROCESS FOR PREPARING A POLYAROMATIC COMPOUND

This application is an application under 35 U.S.C. Section 371 of International Application Number PCT/FR00/03289 filed on Nov. 24, 2000.

The present invention relates to a process for preparing a polyaromatic compound comprising a concatenation of two aromatic cycles and carrying at least one amino group on one of the aromatic cycles.

In particular, the invention relates to a biphenyl type compound, one of the benzene cycles of which carries an amino group.

In the present disclosure of the invention, the term "polycyclic aromatic compound carrying an amino group" means a compound resulting from a concatenation of two aromatic cycles wherein one of the hydrogen atoms of one of the aromatic cycles being replaced by an $NH_2$ group.

The term "aromatic compound" means the conventional notion of aromaticity as defined in the literature, in particular by Jerry MARCH, Advanced Organic Chemistry, 4$^{th}$ Edition, John Wiley & Sons, 1992, pp. 40 ff.

For simplicity, the expression "aryl" designates all aromatic compounds, whether they are carbocyclic aromatic compounds or heterocyclic aromatic compounds.

Biphenyl type structures are encountered in many molecules used in the pharmaceutical field. In particular, a process for preparing compounds of the N-(biaryl)-amine type, in particular N-(biphenyl)-amine is sought.

Michael Hird et al. (Synlett 1999, No. 4, 438–440) have described the preparation of such compounds using a coupling reaction between an arylboronic acid and a halogenoaniline, in the presence of a palladium catalyst complexed with a triphenylphosphine, sodium carbonate, dimethoxyethane and water. That publication mentions that the coupling reaction is accompanied by very substantial deamination of the reactant and of the product formed.

A. D. Hamilton et al. [Journal of Medicinal Chemistry 1996, 39, p. 217–223] recommend coupling a 3-methylphenylarylboronic acid with 4-bromonitrobenzene to produce a nitrobiphenyl. It is then necessary to reduce the nitro group to an amino group using hydrogen in the presence of palladium on charcoal.

D. Badone et al., J. Org. Chem 1997, 62, 7170–7173 have proposed coupling an arylboronic acid with a halogenoaniline, where the amino group is protected by an acetyl group. After the coupling reaction, liberation of the amino group involves a supplemental acid treatment step.

Thus, the provision of a process that can effect direct coupling between an arylamine and an arylboronic acid is desirable.

We have now discovered, and this constitutes the subject matter of the present invention, a process for preparing a polycyclic aromatic compound comprising at least one concatenation of two aromatic cycles and carrying at least one amino group on one of the aromatic cycles, characterized in that it consists of reacting an aromatic compound carrying at least one amino group and a leaving group with an arylboronic acid and/or its derivatives in an aqueous medium and in the presence of an effective quantity of a palladium catalyst.

In accordance with the process of the invention, an aromatic compound carrying at least one amino group and a leaving group is reacted with an arylboronic acid: the reaction takes place in an aqueous medium and in the presence of a palladium catalyst to produce a biphenyl carrying an amino group. This latter is obtained without deamination, which is surprising in view of the descriptions in the literature.

More precisely, the aromatic compound carrying at least one amino group and a leaving group, hereinafter designated an "aminoaromatic compound" has general formula (I):

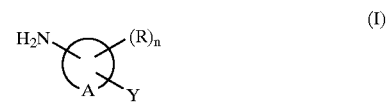

in which:

A designates the residue of a cycle forming all or a portion of an aromatic, monocyclic or polycyclic, carbocyclic or heterocyclic system;

R, which can be identical or different, represents the substituents on the cycle;

Y represents a leaving group, preferably a halogen atom or a sulphonic ester group with formula-$OSO_2$-R, where R is a hydrocarbon group;

n represents the number of substituents on the cycle.

In the formula for the sulphonic ester, R is a hydrocarbon group of any nature containing 1 to 20 carbon atoms. However, given that Y is a leaving group, it is economically advantageous for R to be simple in nature, and more particularly it represents a linear or branched alkyl group containing 1 to 4 carbon atoms, preferably a methyl or ethyl group, but it can also represent, for example, a phenyl or tolyl group or a trifluoromethyl group. A preferred group Y is the triflate group, corresponding to a group R representing a trifluoromethyl group.

Preferred leaving groups are a bromnine or chlorine atom.

The invention is applicable to aminoaromatic compounds with formula (I) in which A is the residue of a cyclic compound preferably containing at least 4 atoms in the cycle, preferably 5 or 6, optionally substituted, and representing at least one of the following cycles:

an aromatic, monocyclic or polycyclic carbocycle;

an aromatic, monocyclic or polycyclic heterocycle containing at least one of heteroatoms O, N or S.

More precisely, and without limiting the scope of the invention, optionally substituted residue A can represent the residue:

1° of an aromatic, monocyclic or polycyclic carbocyclic compound.

The term "polycyclic carbocyclic compound" means:

a compound constituted by at least 2 aromatic carbocycles and forming ortho- or ortho- and peri-condensed systems between them;

a compound constituted by at least 2 carbocycles only one of which is aromatic and forming ortho- or ortho- and peri-condensed systems between them;

2° of an aromatic, monocyclic or polycyclic heterocyclic compound.

The term "polycyclic heterocyclic compound" means:

a compound constituted by at least 2 heterocycles containing at least one heteroatom in each cycle wherein at least one of two cycles is aromatic and forming ortho- or ortho- and peri-condensed systems between them;

a compound constituted by at least one carbocycle and at least one heterocycle wherein at least one of the cycles is aromatic and forming ortho- or ortho- and peri-condensed systems between them.

More particularly, optionally substituted residue A represents one of the following cycles:

an aromatic carbocycle:

an aromatic bicycle comprising two aromatic carbocycles:

a partially aromatic bicycle comprising two carbocycles one of which is aromatic:

an aromatic heterocycle:

an aromatic bicycle comprising an aromatic carbocycle and an aromatic heterocycle:

a partially aromatic bicycle comprising an aromatic carbocycle and a heterocycle:

an aromatic bicycle comprising two aromatic heterocycles:

a partially aromatic bicycle comprising a carbocycle and an aromatic heterocycle:

a tricycle comprising at least one carbocycle or an aromatic heterocycle:

In the process of the invention, an aminoaromatic compound with formula (I) is preferably used in which A represents an aromatic ring, preferably a benzene or naphthalene ring.

The aromatic compound with formula (I) can carry one or more substituents. The substituent can be of any type provided that it does not interfere with the reaction.

The number of substituents present on a cycle depends on the carbon condensation of the cycle and on the presence or absence of unsaturated bonds on the cycle.

The maximum number of substituents that can be carried by a cycle can readily be determined by the skilled person.

In the present text, the term "plurality" generally means less than 4 substituents on an aromatic ring.

Examples of substituents are given below, but this list is not limiting in nature.

Groups R, which may be identical or different, preferably represent one of the following substituents:

a linear or branched alkyl group containing 1 to 6 carbon atoms, preferably 1 to 4 carbon atoms, such as methyl, ethyl, propyl, isopropyl, butyl, isobutyl, sec-butyl or tert-butyl;

a linear or branched alkenyl or alkynyl group containing 2 to 6 carbon atoms, preferably 2 to 4 carbon atoms, such as vinyl or allyl;

a linear or branched alkoxy group containing 1 to 6 carbon atoms, preferably 1 to 4 carbon atoms, such as methoxy, ethoxy, propoxy, isopropoxy, butoxy groups, an alkenyloxy group, preferably an allyloxy group, or a phenoxy group;

a cyclohexyl, phenyl or benzyl group;

an acyl group containing 2 to 6 carbon atoms;

a group with formula:
—$R_1$—OH
—$R_1$—SH
—$R_1$—COOR$_2$
—$R_1$—CO—$R_2$
—$R_1$—CHO
—$R_1$—N=C=O
—$R_1$—N=C=S
—$R_1$—NO$_2$
—$R_1$—CN
—$R_1$—N($R_2$)$_2$
—$R_1$—CO—N($R_2$)$_2$
—$R_1$—SO$_3$M
—$R_1$—SO$_2$M
—$R_1$—X
—$R_1$—CF$_3$ in which formulae, $R_1$ represents a covalent bond or a linear or branched, saturated or unsaturated divalent hydrocarbon group containing 1 to 6 carbon atoms, such as methylene, ethylene, propylene, isopropylene, isopropylidene; groups $R_2$, which may be identical or different, represent a hydrogen atom or a linear or branched alkyl group containing 1 to 6 carbon atoms or a phenyl group; M represents a hydrogen atom, an alkali metal, preferably sodium, or a group $R_2$; and X represents a halogen atom, preferably a chlorine, bromine or fluorine atom.

More particularly, the present invention is applicable to aminoaromatic compounds with formula (I) in which group or groups R represent:

a linear or branched alkyl group containing 1 to 6 carbon atoms, preferably 1 to 4 carbon atoms, such as methyl, ethyl, propyl, isopropyl, butyl, isobutyl, sec-butyl or tert-butyl;

a linear or branched alkenyl group containing 2 to 6 carbon atoms, preferably 2 to 4 carbon atoms, such as vinyl or allyl;

a linear or branched alkoxy group containing 1 to 6 carbon atoms, preferably 1 to 4 carbon atoms, such as methoxy, ethoxy, propoxy, isopropoxy, butoxy groups, an alkenyloxy group, preferably an allyloxy group, or a phenoxy group;

a group with formula:
—$R_1$—OH
—$R_1$—N($R_2$)$_2$
—$R_1$—SO$_3$M in which formulae, $R_1$ represents a covalent bond or a linear or branched, saturated or unsaturated divalent hydrocarbon group containing 1 to 6 carbon atoms, such as methylene, ethylene, propylene, isopropylene, isopropylidene; groups $R_2$, which may be identical or different, represent a hydrogen atom or a linear or branched alkyl group containing 1 to 6 carbon atoms or a phenyl group; M represents a hydrogen atom or a sodium atom.

More preferably, R represents a linear or branched alkyl group containing 1 to 4 carbon atoms, more particularly a methyl group.

In formula (I), n is a number of 4 or less, preferably 1 or 2.

Examples of compounds with formula (I) that can be cited are 4-bromoaniline, 4-bromo-3-methylaniline, 1-amino-3-bromonaphthalene and 2-chloro-3-aminopyridine.

In accordance with the invention, the aminoaromatic compound with formula (I) reacts with an arylboronic acid with formula:

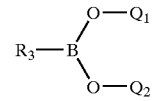

in which:

$R_3$ represents an aromatic, monocyclic or polycyclic carbocyclic or heterocyclic group;

$Q_1$, $Q_2$, which may be identical or different, represent a hydrogen atom, a linear or branched, saturated or unsaturated, aliphatic group containing 1 to 20 carbon atoms, or a group $R_3$;

or $Q_1$ and $Q_2$ can be connected together via an alkylene or alkylenedioxy group containing 1 to 4 carbon atoms;

or $Q_1$ and $Q_2$ can be connected together via —O—B—O— to form a boroxine group with formula (III) in which $R_3$ has the meaning given above:

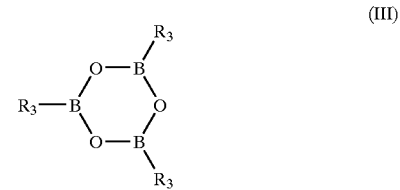

(III)

More precisely, the arylboronic acid has formula (II) or (III) in which group $R_3$ represents an aromatic carbocyclic or heterocyclic group. $R_3$ can take the meanings given above for A. However, more particularly, $R_3$ represents a carbocyclic group such as a phenyl, naphthyl or heterocyclic group such as a pyrrolyl, pyridyl, pyrimidinyl, pyridazinyl, pyrazinyl, 1,3-thiazolyl, 1,3,4-thiadiazolyl or thienyl group.

The aromatic cycle can also be substituted. The number of substituents is generally at most 4 per cycle but is usually equal to 1 or 2. Reference should be made to the definition of R for examples of substituents.

Preferred substituents are alkyl or alkoxy groups containing 1 to 4 carbon atoms, an amino group, a nitro group, a cyano group, a halogen atom or a trifluoromethyl group.

Regarding $Q_1$ and $Q_2$, which can be identical or different, they more particularly represent a hydrogen atom or a linear or branched acyclic aliphatic group containing 1 to 20 carbon atoms, which may be saturated or comprising one or a plurality of unsaturated bonds in their chain, preferably 1 to 3 unsaturated bonds, preferably simple or conjugated double bonds.

$Q_1$, $Q_2$ preferably represent an alkyl group containing 1 to 10 carbon atoms, preferably 1 to 4, or an alkenyl group containing 2 to 10 carbon atoms, preferably a vinyl or 1-methylvinyl group;

$Q_1$, $Q_2$ can take the meanings given for $R_3$, and in particular any cycle can also carry a substituent as described above.

$R_3$ preferably represents a phenyl group.

The scope of the present invention also encompasses arylboronic acid derivatives such as anhydrides and esters, and more particularly alkyl esters containing 1 to 4 carbon atoms.

Examples of arylboronic acids that can be cited are: benzeneboronic acid, 2-thiopheneboronic acid, 3-thiopheneboronic acid, 4-methylbenzeneboronic acid, 3-methylthiophene-2-boronic acid, 3-aminobenzeneboronic acid, 3-aminobenzeneboronic acid hemisulphate, 3-fluorobenzeneboronic acid, 4-fluorobenzeneboronic acid, 2-formylbenzeneboronic acid, 3-formylbenzeneboronic acid, 4-formylbenzeneboronic acid, 2-methoxybenzeneboronic acid, 3-methoxybenzeneboronic acid, 4-methoxybenzeneboronic acid, 4-chlorobenzeneboronic acid, 5-chlorothiphene-2-boronic acid, benzo[b]furane-2-boronic acid, 4-carboxy benzeneboronic acid, 2,4,6-trimethyl benzeneboronic acid, 3-nitrobenzeneboronic acid, 4-(methylthio)benzene boronic acid, 1-naphthaleneboronic acid, 2-naphthaleneboronic acid, 2-methoxy-1-naphthaleneboronic acid, 3-chloro-4-fluorobenzeneboronic acid, 3-acetamidobenzeneboronic acid, 3-trifluoromethylbenzeneboronic acid, 4-trifluoromethylbenzeneboronic acid, 2,4-dichlorobenzeneboronic acid, 3,5-dichlorobenzeneboronic acid, 3,5-bis(trifluoromethyl)benzeneboronic acid, 4,4'-biphenyldiboronic acid, and esters and anhydrides of said acids.

A palladium catalyst is used in the process of the invention.

The palladium can be supplied in the form of a finely divided metal or in the form of an inorganic derivative such as an oxide or a hydroxide. It is possible to use a mineral salt, preferably a nitrate, sulphate, oxysulphate, halide, oxyhalide, silicate or carbonate, or an organic derivative, preferably, a cyanide, oxalate or acetylacetonate; an alcoholate and still more preferably, a methylate or ethylate; or a carboxylate and still more preferably an acetate. Complexes can also be used, in particular chlorine-containing or cyanide-containing complexes of palladium and/or of alkali metals, preferably sodium, potassium or ammonium.

Particular examples of compounds that can be used to prepare the catalysts of the invention that can be cited are:

palladium (0);
palladium (0) dibenzylideneacetone;
palladium (II) bromide;
palladium (II) chloride;
palladium (II) iodide;
palladium (II) cyanide;
hydrated palladium (II) nitrate;
palladium (II) oxide;
dihydrated palladium (II) sulphate;
palladium (II) acetate;
palladium (II) propionate;
palladium (II) butyrate;
palladium (II) benzoate;
palladium (II) acetylacetonate;
ammonium tetrachloropalladate (II);
potassium hexachloropalladate (IV);
palladium (II) tetramine nitrate;
palladium (II) dichlorobis(acetonitrile);
palladium (II) dichlorobis(benzonitrile);
palladium (II) dichloro(1,5-cyclooctadiene);
palladium (II) dichlorodiamine.

If the catalyst is a palladium compound, it can be introduced in the solid form or in an aqueous solution. As an example, palladium chloride, which is preferably selected, can be introduced in the solid form or in solution in an aqueous hydrochloric acid solution (for example 5% or 10%).

The compound in solution can be deposited on a support. Metallic palladium can also be deposited on a support.

The support is selected so that it is inert under the reaction conditions.

Examples of supports that can be employed are mineral or organic supports such as charcoal, activated charcoal, acetylene black, silica, alumina, clays, and more particularly, montmorillonite or equivalent materials or organic polymers, for example the polyvinyl polymers PVC (polyvinyl chloride) or PVDC (polyvinylidenechloride), or polystyrene polymers that may be functionalised with nitrile functions, or polyacrylic polymers (in particular polyacrylonitrile).

In general, the metal is deposited in an amount of 0.5% to 10%, preferably 1% to 5% by weight of catalyst.

Of the catalysts cited above, the preferred catalyst is palladium chloride, palladium acetate or palladium deposited on charcoal.

The catalyst can be employed in the form of a powder, pellets or granules.

In accordance with the process of the invention, compounds (I) and (II) are reacted in the presence of a base.

The bases used are alkali metal hydroxides, preferably sodium or potassium; alkaline-earth metal hydroxides, preferably calcium; or ammonium hydroxide; alkali metal carbonates or bicarbonates, preferably sodium or potassium carbonate; metal phosphates, preferably sodium or potassium carbonate. It is also possible to use an amine, preferably a secondary or tertiary amine. The following can in particular be cited: diisopropylamine, pyrrolidine, morpholine, triethylamine, triethanolamine, diisopropylamine.

In accordance with the process of the invention, the aminoaromatic compound and arylboronic acid can advantageously be reacted in an aqueous medium in the proportions mentioned below and in the presence of a palladium catalyst and a base.

The quantity of reactants employed is such that the mole ratio of arylboronic acid/aromatic compound is advantageously 1 or more, and is preferably in the range 1 to 1.2.

The quantity of catalyst employed, expressed as the mole ratio of the metal to the arylboronic acid, is between $5 \times 10^{-7}$ and 0.2.

The quantity of base employed, expressed as the ratio between the number of moles of OH and the number of moles of arylboronic acid, is preferably between 2 and 4, more particular about 2.

The quantity of water added is such that the medium can be stirred. It is advantageously in the range 10% to 200% by weight of the reaction medium. The water is generally supplied by the base.

The reaction temperature is advantageously in the range from ambient temperature (usually between 15° C. and 25° C.) to 130° C., preferably in the range 50° C. to 100° C.

Generally, the reaction is carried out under autogenous pressure of the reactants.

In a preferred variation of the process of the invention, the process of the invention is carried out in a controlled atmosphere of inert gases. An atmosphere of rare gases can be established, preferably argon, but it is cheaper to use nitrogen.

From a practical viewpoint, the process is simple to carry out. All of the reactants are charged and heated for the period required for the reaction to be completed.

The polycyclic aromatic compound is recovered conventionally, for example by extraction using an organic solvent; ether-oxides can be cited, preferably isopropyl ether; aliphatic or aromatic hydrocarbons, which may or may not be halogenated, preferably toluene.

A polyaromatic compound is obtained that can be represented by formula (IV):

(IV)

in which formula (IV), A, R, $R_3$ and n have the meanings given above.

More particularly, the invention is applicable to preparing 4-phenyl-3-methylaniline.

Non-limiting examples will now be given by way of illustration only.

In the example, a yield (RT) is defined corresponding to the ratio between the number of moles of product formed and the number of moles of substrate transformed.

EXAMPLE 1

The following were charged into a 500 ml reactor provided with a coolant, a magnetic stirrer, a thermocouple and a nitrogen atmosphere:

28.8 g (150 mmole) of 97% 4-bromo-3-methylaniline;
21.1 g (153 mmole) of 100% potassium carbonate;
19.2 g (154 mmole) of 97% phenylboronic acid;
10 mg (0.056 mmole) of palladium chloride;
200 g (11.1 mole) of water, degassed conventionally by bubbling with nitrogen.

The reactants were charged into the reactor and heated under reflux (100° C.) with stirring and under nitrogen.

The reaction was complete after 1 h 30.

Extraction was carried out with isopropyl ether (100 ml).

It was quickly decanted.

The organic phase was washed with 2×30 ml of water.

It was dried over magnesium sulphate then concentrated by evaporation.

High performance liquid chromatography analysis measured 28 g of 4-phenyl-3-methylaniline, corresponding to a 100% yield.

EXAMPLE 2

The following were charged into a 1000 ml reactor provided with a coolant, a magnetic stirrer, a thermocouple and a nitrogen atmosphere:

38.56 g (300 mmole) of 4-chloro-3-aminopyridine;
42.2 g (306 mmole) of 100% potassium carbonate;
38.4 g (308 mmole) of 97% phenylboronic acid;
20 mg (0.112 mmole) of palladium chloride;
400 g (22.2 mole) of degassed water.

The reactants were charged into the reactor and heated under reflux (100° C.) with stirring and under nitrogen.

The reaction was complete after 3 h.

Extraction was carried out with isopropyl ether (200 ml).

It was quickly decanted.

The organic phase was washed with 2×60 ml of water.

It was dried over magnesium sulphate then concentrated by evaporation.

High performance liquid chromatography analysis measured 51 g of 4-phenyl-3-methylaniline, corresponding to a yield of close to 100%.

What is claimed is:

1. A process for preparing a polycyclic aromatic compound having at least one concatenation of two aromatic cycles and carrying at least one amino group on one of the aromatic cycles, comprising the step of reacting an aromatic compound carrying at least one amino group and a leaving group with an arylboronic acid or a derivative thereof, in an aqueous medium, and in the presence of an effective quantity of a palladium catalyst.

2. The process according to claim 1, wherein the aromatic compound carrying at least one amino group has the following formula (I):

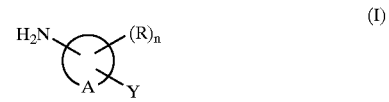

(I)

wherein:
A designates the residue of a cycle forming all or a portion of an aromatic, monocyclic or polycyclic, carbocyclic or heterocyclic, group;
R, which is identical or different, represents substituents on the cycle;
Y is leaving group; and
n represents the number of substituents on the cycle.

3. The process according to claim 2, wherein Y is halogen atom or a sulphonic ester group with formula —$OSO_2$—R', wherein R' is a hydrocarbon group, or a trifluoromethyl group.

4. The process according to claim 3, wherein Y is a bromine atom, a chlorine atom or a sulphonic ester with formula —$OSO_2$—R', wherein R' is a linear or branched alkyl group having 1 to 4 carbon atoms.

5. The process according to claim 3, wherein R' is a methyl group, an ethyl group, a phenyl group, or a tolyl group.

6. The process according to 2, wherein A designates the residue of a cycle having 5 or 6 carbon atoms, optionally substituted, selected from the group consisting of the following cycles:
aromatic, monocyclic or polycyclic carbocycles; and
aromatic, monocyclic or polycyclic heterocycles having at least one O, N or S heteroatom.

7. The process according to claim 2, wherein A designates the residue of a cycle being:
an aromatic carbocycle,
an aromatic bicycle having two aromatic carbocycles,
a partially aromatic bicycle having two carbocycles one of which being aromatic,
an aromatic heterocycle,
an aromatic bicycle having an aromatic carbocycle and an aromatic heterocycle,
a partially aromatic bicycle having an aromatic carbocycle and a heterocycle,
an aromatic bicycle having two aromatic heterocycles, a partially aromatic bicycle having a carbocycle and an aromatic heterocycle, or a tricycle having at least one carbocycle or an aromatic heterocycle.

8. The process according to claim 2, wherein A represents a benzene ring or a naphthalene ring.

9. The process according to claim 2, wherein the aromatic compound carrying at least one amino group of formula (I) has one or more substituent R selected from the group consisting of:

linear or branched alkyl groups containing 1 to 6 carbon atoms;

linear or branched alkenyl or alkynyl groups containing 2 to 6 carbon atoms;

linear or branched alkoxy groups containing 1 to 6 carbon atoms;

alkenyloxy groups;

cyclohexyl group, phenyl group benzyl group;

acyl groups containing 2 to 6 carbon atoms; and a group with formula:
—$R_1$—OH,
—$R_1$—SH,
—$R_1$—COOR$_2$,
—$R_1$—CO—$R_2$,
—$R_1$—CHO,
—$R_1$—N=C=O,
—$R_1$—N=C=S,
—$R_1$—NO$_2$,
—$R_1$—CN,
—$R_1$—N($R_2$)$_2$,
—$R_1$—CO—N($R_2$)$_2$,
—$R_1$—SO$_3$M,
—$R_1$—SO$_2$M,
—$R_1$—X, or
—$R_1$—CF$_3$, wherein $R_1$ represents a covalent bond or a linear or branched, saturated or unsaturated, divalent hydrocarbon group containing 1 to 6 carbon atoms;

$R_2$, which is identical or different, represents a hydrogen atom, a linear or branched alkyl group containing 1 to 6 carbon atoms, or a phenyl group;

M represents a hydrogen atom, an alkali metal, or a group $R_2$;

and X represents a halogen atom.

10. The process according to claim 9, wherein R is selected from the group consisting of:

methyl group, ethyl group, propyl group, isopropyl group, butyl group, isobutyl group, sec-butyl group, tert-butyl group;

vinyl group, allyl group;

methoxy group, ethoxy group, propoxy group, isopropoxy group, butoxy group, an allyloxy group, a phenoxy group; and a group with formula:
—$R_1$—OH,
—$R_1$—SH,
—$R_1$—COOR$_2$,
—$R_1$—CO—$R_2$,
—$R_1$—CHO,
—$R_1$—N=C=O,
—$R_1$—N=C=S,
—$R_1$—NO$_2$,
—$R_1$—CN,
—$R_1$—N($R_2$)$_2$,
—$R_1$—CO—N($R_2$)$_2$,
—$R_1$—SO$_3$M,
—$R_1$—SO$_2$M,
—$R_1$—X, or
—$R_1$—CF$_3$, wherein $R_1$ represents methylene group, ethylene group, propylene group, isopropylene group, isopropylidene group;

$R_2$, which is identical or different, represents a hydrogen atom, a linear or branched alkyl group containing 1 to 6 carbon atoms, or a phenyl group;

M represents a hydrogen atom, sodium, or a group $R_2$;

and X represents a chlorine, bromine or fluorine atom.

11. The process according to claim 2, wherein n is 4 or less.

12. The process according to claim 11, wherein n is 1 or 2.

13. The process according to claim 2, wherein the aromatic compound carrying at least one amino group is 4-bromoaniline, 4-bromo-3-methylaniline, 1-amino-3-bromonaphthalene or 2-chloro-3-aminopyridine.

14. The process according to claim 1, wherein the arylboronic acid has the following formula (II):

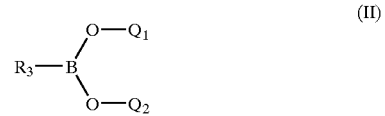

(II)

wherein:

$R_3$ represents an aromatic, monocyclic or polycyclic, carbocyclic or heterocyclic, group;

$Q_1$, $Q_2$, which are identical or different, represent a hydrogen atom, a linear or branched, saturated or unsaturated, aliphatic group containing 1 to 20 carbon atoms, or a group $R_3$;

$Q_1$ and $Q_2$ can be connected together by an alkylene or alkylenedioxy group containing 1 to 4 carbon atoms;

$Q_1$ and $Q_2$ can be connected together via —O—B—O to form a boroxine group with the following formula (III) wherein $R_3$ has the meaning given above:

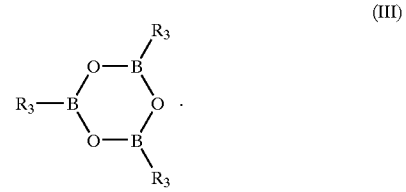

(III)

15. The process according to claim 14, wherein the arylboronic acid has formula (II) or (III), wherein $R_3$ represents phenyl group, naphthyl group, pyrrolyl group, pyridyl group, pyrimidinyl group, pyridazinyl group, pyrazinyl group, 1,3-thiazolyl group, 1,3,4-thiadiazolyl group or thienyl group.

16. The process according to claim 14, wherein the arylboronic acid comprises an aromatic cycle carrying at least one substituent selected from the group consisting of alkyl or alkoxy groups containing 1 to 4 carbon atoms, amino groups, nitro group, cyano group, halogen atoms and trifluoromethyl group.

17. The process according to claim 14, wherein the arylboronic acid has formula (II), wherein $Q_1$, and $Q_2$, which are identical or different, represent a hydrogen atom, a linear or branched acyclic aliphatic group containing 1 to 20 carbon atoms, saturated or having one or more unsaturated bond, or a group $R_3$.

18. The process according to claim 17, wherein $Q_1$ and $Q_2$, which are identical or different represent hydrogen atom or phenyl group.

19. The process according to claim 14, wherein the arylboronic acid is benzeneboronic acid, 2-thipheneboronic acid, 3-thipheneboronic acid, 4-methylbenzeneboronic acid, 3-methylthiophene-2-boronic acid, 3-aminobenzeneboronic acid, 3-aminobenzeneboronic acid hemisulphate, 3-fluorobenzeneboronic acid, 4-fluorobenzeneboronic acid, 2-formylbenzeneboronic acid, 3-formylbenzeneboronic acid, 4-formylbenzeneboronic acid, 2-methoxybenzeneboronic acid, 3-methoxybenzeneboronic acid, 4-methoxybenzeneboronic acid, 4chlorobenzeneboronic acid, 5-chlorothiphene-2-boronic acid, benzo[b]furane-2-boronic acid, 4-carboxybenzeneboronic acid, 2,4,6-trimethylbenzeneboronic acid, 3-nitrobenzeneboronic acid, 4-(methylthio)benzeneboronic acid, 1-naphthaleneboronic acid, 2-naphthaleneboronic acid, 2-methoxy-1-naphthaleneboronic acid, 3-chloro-4-fluorobenzeneboronic acid, 3-acetamidobenzeneboronic acid, 3-trifluoromethylbenzeneboronic acid, 4-trifluoromethylbenzeneboronic acid, 2,4-dichlorobenzeneboronic acid, 3,5-dichlorobenzeneboronic acid, 3,5-bis(trifluoromethyl)benzeneboronic acid, 4,4'-biphenyldiboronic acid, an ester of said acids, or an anhydride of said acids.

20. The process according to claim 1, wherein the palladium catalyst comprises palladium supplied in the form of a finely divided metal, in the form of an inorganic derivative, in the form of an organic derivative, or in the form of a chlorine-containing or cyanide-containing complex of palladium and optionally of alkali metals.

21. The process according to claim 20, wherein the alkali metal is sodium, potassium or ammonium.

22. The process according to claim 20, wherein the inorganic derivative is an oxide, a hydroxide, or a mineral salt.

23. The process according to claim 22, wherein the mineral salt is a salt of a nitrate, sulphate, oxysulphate, halide, oxyhalide, silicate or carbonate.

24. The process according to claim 20 wherein the organic derivative is a cyanide, an oxalate, an acetylacetonate, an alcoholate, or a carboxylate.

25. The process according to claim 24, wherein the organic derivative is a methylate, an ethylate or an acetate.

26. The process according to claim 20, wherein the palladium is in a metallic form, or is deposited on a support, or in the form of a compound in solution.

27. The process according to claim 20, wherein the palladium catalyst is palladium chloride, palladium acetate or palladium deposited on charcoal.

28. The process according to claim 1, wherein the aqueous medium comprises a base being an alkali metal, an alkaline-earth hydroxide, an ammonium hydroxide, an alkali metal carbonate, an alkali metal bicarbonate, a metal phosphate, a secondary amine, or a tertiary amine.

29. The process according to claim 28, wherein the base is potassium carbonate, sodium phosphate or potassium phosphate.

30. The process according to claim 1, wherein the aqueous medium comprises water, in a quantity representing 10% to 200% by weight of the reactive compounds.

31. The process according to claim 1, wherein the reaction is carried out at a temperature of from ambient temperature to 130° C.

32. The process according to claim 31, wherein the temperature is of from 50° C. to 100° C.

33. The process according to claim 1, wherein the polycyclic aromatic compound is 4-phenyl-3-methylaniline.

* * * * *